United States Patent [19]

Corbellini et al.

[11] 4,128,567

[45] Dec. 5, 1978

[54] ALUMINIUM POLYMERIC COMPOUNDS OF POLYIMINE NATURE

[75] Inventors: Margherita Corbellini, Milan; Agostino Balducci, San Donato Milanese, both of Italy

[73] Assignee: Snamprogetti, S.p.A., Milanese, Italy

[21] Appl. No.: 750,542

[22] Filed: Dec. 14, 1976

Related U.S. Application Data

[63] Continuation of Ser. No. 592,222, Jul. 1, 1975, abandoned.

[30] Foreign Application Priority Data

Jul. 1, 1974 [IT] Italy .............................. 24661 A/74

[51] Int. Cl.² .............................................. C07F 5/06
[52] U.S. Cl. ............................ 260/448 R; 252/431 N; 528/9
[58] Field of Search .......................... 260/448 R, 2 M

[56] References Cited

U.S. PATENT DOCUMENTS

| 3,255,169 | 6/1966 | Kearby | 260/93.7 |
| 3,651,064 | 3/1972 | Nelson et al. | 260/448 R |
| 3,781,318 | 12/1973 | Corbellini et al. | 260/448 R |
| 3,983,150 | 9/1976 | Casensky et al. | 260/448 R |

OTHER PUBLICATIONS

Ehrlich et al., Inorg. Chem. V3, No. 5, pp. 628-631, (1964).
Laubengayer et al., JACS 83, pp. 542-546, (1961).
Laubengayer et al., Inorg. Chem. V1, No. 3, pp. 632-637, (1962).

Primary Examiner—Helen M. S. Sneed
Attorney, Agent, or Firm—Morgan, Finnegan, Pine, Foley & Lee

[57] ABSTRACT

The present specification describes novel aluminum-polyimine compounds that are useful as catalysts for the polymerization of unsaturated compounds. The aluminum-polyimine compounds are of the formula:

$$Al_h (NR)_k H_i Y_j$$

in which R is an aliphatic, aromatic or cycloaliphatic hydrocarbon radical, H is hydride hydrogen, Y is halogen, k ranges from 2 to 50, h/k 1, (i+j)/h 1, i≠0 and j≧0.

6 Claims, No Drawings

ALUMINIUM POLYMERIC COMPOUNDS OF POLYIMINE NATURE

This is a continuation of application Ser. No. 592,222 filed July 1, 1975, now abandoned.

The present invention relates to new aluminum compounds of polyimine nature, to the process for the preparation thereof and also to processes making use of these compounds as components of catalytic systems to be employed in the polymerization of unsaturated compounds.

It is known, from U.S. Pat. No. 3,875,133 there are aluminum derivatives of polyimine nature containing halogen atoms bound to aluminum.

Moreover the same Applicant owns two copending patent applications Ser. No. 524,312, filed Nov. 15, 1974 now U.S. Pat. No. 4,022,809 issued May 10, 1977 and Ser. No. 592,247, filed July 1, 1975 now U.S. Pat. No. 4,032,553 issued June 28, 1977, relating to oligomer N-alkyl-iminoalanes having chemical compositions, respectively $$-[AlX - NR]_n-$$ (a)

and $$(X-Al\ NR)_x\ (XYAl)_y\ (NHR)_y$$ (b)

in which X and Y, the same or different, mean hydride hydrogen and/or halogen atoms directly bound to aluminum, n is an integer lower than or equal to 10, the (x + y) sum is an integer lower than or equal to 10, y is an integer different from zero, R is an aliphatic, aromatic or cycloalyphatic hydrocarbon, characterized by a tridimensional structure and atomic ratios $X/Al = 1$ and $N/Al = 1$ as to (a) and $(X + Y)/Al > 1$ and $N/Al = 1$ as to (b).

Some of these compounds, if employed as components of catalytic systems together with transition metal derivatives in the polymerization of coniugated dienes, allow the polymerization reaction to be carried out at a polymerization rate higher then those obtainable by other catalyst systems and, at the same time, side reactions or cyclizations of the polymeric chains can be avoided. Inter alia, this allows to obtain polymer at lower consumptions of transition metal derivatives.

We have now found, that the abovesaid aluminum compounds may be modified through a reaction with alkaline or alkaline-earth metal alanate, or with aluminum hydride complexes to give new aluminum derivatives having a substantial polyimine nature, that form a further object of the present invention and, besides preserving or improving the abovesaid characteristics in the polymerization of conjugated dienes, may be employed as components of catalytic systems in the polymerization of other unsaturated compounds, particularly of ethylene and mono-olefins.

The aluminum compounds, according to the present invention, have the following general formula $$Al_h\ (NR)_k\ H_i\ Y_j$$

in which R is an aliphatic, aromatic or cycloaliphatic hydrocarbon radical, H is hydride hydrogen, Y is halogen, k ranges from 2 to 50, $h/k > 1$, $(i + j)/h > 1$, $i \neq 0$ and $j \geq 0$.

As abovesaid, the inventive aluminum compounds are obtained by reacting the cited polyimine compounds with alkaline or alkaline-earth metal alanates or with aluminum hydride complexes.

According to the employed starting compounds, hydrogen development can take place and/or the alkaline metal halide may separate.

The reaction easily occurs at temperatures ranging from 0° to 70° C and, preferably, at pressures equal to the vapor pressure of the solvent, in which the operations are carried out, at the working temperature.

Use may be made of solvents belonging to the class of ethers such as, for instance, dimethyl ether, diethyl ether, methyl ethyl ether, cyclic ethers or mixtures thereof with hydrocarbons or hydrocarbons only. As aforesaid the inventive compounds are useful components of catalytic systems for the polymerization of compounds having at least an olefine unsaturation together with a transition metal compound.

Therefore they can be used to give catalysts that are not self-inflammable in the presence of air as are the aluminum alkyls.

EXAMPLES (1) 26 mmoles of LiAlH$_4$ in an ether solution (1 M) were added, over 5 minutes to 176 mg atoms of polyiminoalane (as Al), dissolved in 300 ml of an ether-heptane mixture (30% as ethyl ether), having $Cl/Al = 0.26$, $N/Al = 0.97$, the addition being performed at 45° C and under stirring. These conditions were kept for 4 hours, then the whole was filtered on a sintered glass septum. All operations were carried out under an inert and anhydrous atmosphere.

The filtrate was distilled under vacuum in order to eliminate ethyl ether and heptane was added. cycloaliphatic characterized 1 1 Y)/Al=1 1

The solution, after analysis, had the following composition $$Al_1H_{1.25}N_{0.9}Cl_{0.1}$$

(2) 28 mmoles of NaAlH$_4$ suspended in ethyl ether were added to 187 mmoles of polyiminoalane (as Al) dissolved in 300 ml of an ether-hexane mixture (30% as ethyl ether) having $Cl/Al = 0.26$ $N/Al = 0.97$, the addition being performed under stirring and at a temperature of 45° C. The whole was kept under these conditions for 4 hours and then was filtered from sodium chloride.

The filtrate was distilled under vacuum in order to eliminate ethyl ether and heptane was added. The solution, after analysis had the following composition Al = 0.724 mole/liter; H = 0.864 mole/liter
N = 0.602 mole/liter
Cl = 0.095 mole/liter
corresponding to the raw formula $$Al_1N_{0.83}H_{1.19}Cl_{0.13}$$

(3) 25 mmoles of NaH were added, under stirring at 45° C, to 180 mg atoms of polyiminoalane (as Al) dissolved in 300 ml of an ether-heptane mixture and having $Cl/Al = 0.25$, $N/Al = 0.86$. The whole was kept under these conditions for 4 hours, then was cooled and filtered on sintered septum. The filtrate was distilled under vacuum in order to eliminate ethyl ether and heptane was added. The solution, analyzed, had the following composition Al = 0.95 mole/liter N = 0.82 mole/liter
Cl = 0.10 mole/liter
H = 1.10 mole/liter
corresponding to the raw formula $$Al_1N_{0.86}H_{1.16}Cl_{0.11}$$

(4) An ether solution of polyiminoalane, having a N/Al molar ratio equal to 1, no chlorine and containing 30.78 mg atoms of aluminum, was added with an ether solution of anhydrous HCl in such an amount to have a molar ratio Al/Al = 0.165, then were added 6.05 ml of an ether solution of LiAlH$_4$ having a concentration 0.824 M (4.98 mmoles). The whole was stirred for 1 hour and then kept resting over 20 hours.

LiCl was filtered and the solution was made free from the solvent through a distillation under vacuum. The solid residual was long dried under vacuum at room temperature and analyzed Al, 33.25%; N, 14.90%, H,14.88 meq/g corresponding to the raw formula $$Al_1 N_{0.86}H_{1.22}$$

The obtained product was soluble in aromatic an cycloaliphatic hydrocarbon solvents.

(5) An ether solution of AlH$_3$. Et$_2$O (6.2 mmoles) was added to an ether-hexane solution (30% as ethyl ether) of polyiminoalane having molar ratios N/Al = 0.99, Cl/Al = 0.10 containing 42.7 mg atoms of aluminum.

It was kept boiling, under stirring, for 4 hours, then the solvent was removed under vacuum and hexane was replaced by ethyl ether. Since the solution was lightly cloudy, it was filtered.

At analysis there was $$Al_1N_{0.88}Cl_{0.09}H_{1.15}$$

Polymerization examples: ethylene (1) A 5 l autoclave equipped with an anchor stirrer was charged with 2 l of anhydrous and air-free n-heptane, then it was thermostated at 90° C. Then the catalyst, prepared aside, was added, it being constituted by 1.00 g of TiCl$_3$.AA corresponding to 2.5 mg at/liter and 1.27 g of polyiminoalane (PIAPE) synthetized according to one of the abovesaid recipes corresponding to 7.5 mg at/1 of H.

3 atmospheres of H$_2$ were sent, as molecular weight regulator, then ethylene was sent up to a total pressure of 5 atomspheres, the pressure being kept at such a value by the running itself of the polymerization reaction.

After two hours reaction, the autoclave was open, the suspension was centrifugated and the polymer was dried under vacuum at 60° C.

750 g of polymer were obtained having d = 0.958 and MFI = 0.720.

A polymerization test, carried out in the same conditions by using a polyiminoalane with N/Al = 1 according to Italian Pat. No. 885.567, gave g 250 of polymer having MFI = 0.70

(2) The formalities of the foregoing example were followed by using 5 atmospheres of hydrogen. 550 g were obtained of a polymer having MFI=3.60.

Polymerization example: isoprene (1) 90 ml of anhydrous and air-free hexane, 1.82. 10$^{-3}$ mole of TiCl$_4$ and PIAPE in such amounts to have the Al/Ti ratio: 0.95 1 1.05 1.1 1.2, were introduced into a series of bottles. These were sealed and the catalyst was aged; then were added 30 ml of anhydrous freshly distilled isoprene. The bottles were sealed by crown plugs and put in a thermostat at 30° C. All operations were carried out under inert atmosphere.

After two hours polymerization, the reaction was stopped by an addition of ethyl alcohol and an ethyl alcohol coagulation was performed.

After drying, the following conversions were obtained:

| Al/Ti | Conversion % g as dry polymer |
|---|---|
| 1.00 | 35 |
| 1.05 | 90 |
| 1.10 | 60 |
| 1.20 | 45 |

A comparative serie of polymerization, carried out again by using PIA according to Italian Patent 885.567, gave the following results:

| Al/Ti | Conversion % g as dry polymer |
|---|---|
| 1.00 | 25 |
| 1.05 | 86 |
| 1.10 | 75 |
| 1.20 | 52 |

Obtained polyisoprenes had a 1.4 cis content hygher than 95%.

Copolymerizatioh examples: monoolefins (1) A 5 l autoclave, provided with an anchor stirrer, was charged with 2 l of anhydrous and air-free n-heptane containing 15 g of anhydrous and air-free hexene-1; it was thermostated at 85° C, then charged with the performed catalyst constituted by 1.00 g of TiCl$_3$ AA corresponding to 2.5 mg atoms/liter and 0.9 g of polyiminoalane (PIA-PE) corresponding to 5 mg atoms/liter as H. H$_2$ was sent, as molecular weight regulator, at 2 atm pressure, then ethylene was sent up to a total pressure of 5 atmospheres and such value was kept by an ethylene flow regulated by the running itself of the polymerization reaction. After two hours polymerization, during which were fed 20 g of hexene-1, the reaction was stopped by 250 ml of ethyl alcohol which too solubilized the catalyst.

The suspension was centrifugated and the polymer was dried under vacuum.

620 g of a copolymer were obtained, it having an ash content equal to 300 ppm, d = 0.947 g/cm$^3$, MFI = 0.20 g/10', ESCR>430 hours (environmental stress-cracking resistance).

What we claim is:

1. An aluminum polymeric compound of polyimine nature having the general formula $$Al_h (NR)_k H_i Y_j I$$

wherein R is an aliphatic, aromatic or cycloaliphatic hydrocarbon radical, H is hydride hydrogen, Y is halogen, K ranges from 2 to 50, h/k > 1, (i + j) /h > 1, 1 ≠ 0 and j ≧ 0, compound I being prepared by reacting an aluminum compound of polyimine nature selected from the group having the chemical compositions $$\vphantom{X}+ XAl - NR +_n ( XAl - NR)_{\bar{n}} \qquad (a) (a)$$

and $$(X\text{-}Al\text{-}NR)_x \, (XYAl)_y \, (NHR)_y \quad (b)$$

wherein X and Y, the same or different, mean hydride hydrogen and/or halogen atoms directly bound to aluminum, n is an integer lower than or equal to 10, the (x+y) sum is an integer lower than or equal to 10, y is an integer higher than zero and R is an aliphatic, aromatic or cycloaliphatic hydrocarbon radical, characterized by a tridimensional structure and atomic ratios X/Al=1 and N/Al=1 as to (a) and (X+Y)/Al=1 and N/Al=1 as to (b) with alkali or alkaline-earth metal alanates or with aluminum hydride complexes.

2. An aluminum polymeric compound of polyimine nature having the general formula $$Al_h \, (NR)_k \, H_i \, Y_j \, I$$

wherein R is an aliphatic, aromatic or cycloaliphatic hydrocarbon radical, H is hydride hydrogen, Y is halogen, k ranges from 2 tp 50, h/k > 1, 1, (i + j)/h > 1, i ≠ 0 and j ≧ 0, compound I being prepared by reacting an aluminum compound of polyimine nature selected from the group having the chemical compositions $$-\!\!+\!XAl\text{-}NR\,\rightarrow_n \quad (a)$$

and $$(X\text{-}Al\text{-}NR)_x \, (XYAl)_y \, (NHR)_y \quad (b)$$

wherein X and Y, the same or different, means hydride hydrogen and/or halogen atoms directly bound to aluminum, n is an integer lower than or equal to 10, the (x+y) sum is an integer lower than or equal to 10, y is an integer higher than zero and R is an aliphatic, aromatic or cycloaliphatic hydrocarbon radical, characterized by a tridimensional structure and atomic ratios X/Al=1 and N/Al=1 as to (a) and (X+Y)/Al=1 and N/Al=1 as to (b) with alkali or alkaline-earth metal alanates or with aluminum hydride complexes wherein compound I comprises Al, N, H and Cl in the relative atomic proportions 1:0.9 : 1.25 : 0.1, respectively.

3. An aluminum polymeric compound of polyimine nature having the general formula $$Al_h \, (NR)_k \, H_i \, Y_j \, I$$

wherein R is an aliphatic, aromatic or cycloaliphatic hydrocarbon radical, H is hydride hydrogen, Y is halogen, k ranges from 2 to 50, h/k > 1, 1, (i + j)/h > 1, i ≠ 0 and j ≧ 0, compound I being prepared by reacting an aluminum compound of polyimine nature selected from the group having the chemical compositions $$-\!\!+\!AXl\text{-}NR\,\rightarrow_n \quad (a)$$

and $$(X\text{-}Al\text{-}NR)_x \, (XYAl)_y \, (NHR)_y \quad (b)$$

wherein X and Y, the same or different, mean hydride hydrogen and/or halogen atoms directly bound to aluminum, n is an integer lower than or equal to 10, the (x+y) sum is an integer lower than or equal to 10, y is an integer higher than zero and R is an aliphatic, aromatic or cycloaphatic hydrocarbon radical, characterized by a tridimensional structure and atomic ratios X/Al=1 and N/Al=1 as to (a) and (X+Y)/Al=32 1 and N/Al=1 as to (b) with alkali or alkaline-earth metal alanates or with aluminum hydride complexes wherein compound I comprises Al, N, H and Cl in the relative atomic proportions 1:0.83 : 1.19 : 0.13, respectively.

4. An aluminum polymeric compound of polyimine nature having the general formula $$Al_h \, (NR)_k \, H_i \, Y_j \, I$$

wherein R is an aliphatic, aromatic or cycloaliphatic hydrocarbon radical, H is hydride hydrogen, Y is halogen, k ranges from 2 to 50, h/k > 1, (i + j)/h > 1, i ≠ 0 and j ≧ 0, compound I being prepared by reacting an aluminum compound of polyimine nature selected from the group having the chemical compositions $$-\!\!+\!XAl\text{-}NR\,\rightarrow_n \quad (a)$$

and $$(X\text{-}Al\text{-}NR)_x \, (XYAl)_y \, (NHR)_y \quad (b)$$

wherein X and Y, the same or different, mean hydride hydrogen and/or halogen atoms directly bound to aluminum, n is an integer lower than or equal to 10, the (x+v) sum is an integer lower than or equal to 10, y is an integer higher than zero and R is an aliphatic, aromatic or cycloaliphatic hydrocarbon radical, characterized by a tridimensional structure and atomic ratios X/Al=1 and N/Al=1 as to (a) and (X+Y)/Al=1 as to (b) with alkali or alkaline-earth metal alanates or with aluminum hydride complexes wherein compound I comprises Al, N, H and Cl in the relative atomic proportions 1:0.86 : 1.16 : 0.11, respectively.

5. An aluminum polymeric compound of polyimine nature having the general formula $$Al_h \, (NR)_k \, H_i \, Y_j \, I$$

wherein R is an aliphatic, aromatic or cycloaliphatic hydrocarbon radical, H is hydride hydrogen, Y is halogen, k ranges from 2 to 50, h/k > 1, (i + j)/h > 1, i ≠ 0 and j ≧ 0, compound I being prepared by reacting an aluminum compound of polyimine nature selected from the group having the chemical composition $$-\!\!+\!XAl\text{-}NR\,\rightarrow_n \quad (a)$$

and $$(X\text{-}Al\text{-}NR)_x \, (XYAl)_y \, (NHR)_y \quad (b)$$

wherein X and Y, the same or different, mean hydride hydrogen and/or halogen atoms directly bound to aluminum, n is an integer lower than or equal to 10, the (x+y) sum is an integer lower than or equal to 10, y is an integer higher than zero and R is an aliphatic, aromatic or cycloaliphatic hydrocarbon radical, characterized by a tridimensional structure and atomic ratios X/Al=1 and N/Al=1 as to (a) and (X+Y)/Al=1 and N/Al=1 as to (b) with alkali or alkaline-earth metal alanates or with aluminum hydride complexes wherein compound I comprises Al, N and H in the relative atomic proportions 1:0.86 : 1.22, respectively.

6. An aluminum polymeric compound of polyimine nature having the general formula $$Al_h \, (NR)_k \, H_i \, Y_j \, I$$

wherein R is an aliphatic, aromatic or cycloaliphatic hydrocarbon radical, H is hydride hydrogen, Y is halogen, k ranges from 2 to 50, $h/k > 1$, $(i + j)/h > 1$, $i \neq 0$ and $j \geq 0$, compound I being prepared by reacting an aluminum compound of polyimine nature selected from the group having the chemical compositions

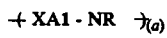

and

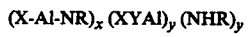

wherein X and Y, the same or different, mean hydride hydrogen and/or halogen atoms directly bound to aluminum, n is an integer lower than or equal to 10, the $(x+y)$ sum is an integer lower than or equal to 10, y is an integer higher than zero and R is an aliphatic, aromatic or cycloaliphatic hydrocarbon radical, characterized by a tridimensional structure and atomic ratios X/Al=1 and N/Al=1 as to (a) and $(X+Y)/Al=1$ and N/Al=1 as to (b) with alkali or alkaline-earth metal alanates or with aluminum hydride complexes wherein compound I comprises Al, N, H and Cl in the relative atomic proportions 1:0.88 : 1.15 : 0.09, respectively.

* * * * *